United States Patent [19]

Obitz

[11] Patent Number: 4,530,843

[45] Date of Patent: Jul. 23, 1985

[54] ISOINDOLE AMIDOXIME DERIVATIVES

[75] Inventor: Daniel Obitz, Antony, France

[73] Assignee: Synthelabo, Paris, France

[21] Appl. No.: 545,159

[22] Filed: Oct. 25, 1983

Related U.S. Application Data

[62] Division of Ser. No. 381,749, May 25, 1982, Pat. No. 4,438,121.

[30] Foreign Application Priority Data

May 25, 1982 [FR] France .................... 81 10428

[51] Int. Cl.³ .................... A61K 31/40; A61K 31/47; C07D 209/46; C07D 209/48
[52] U.S. Cl. .................... 514/416; 546/141; 546/157; 546/158; 548/305; 548/472; 548/477; 548/486; 548/491; 514/417; 514/309; 514/312; 514/392
[58] Field of Search ............... 546/141; 548/472, 477; 424/274

[56] References Cited

U.S. PATENT DOCUMENTS 2,425,288 8/1947 Tryon .................... 548/478
3,635,974 1/1972 Freter et al. .................... 548/472
4,438,121 3/1984 Obitz .................... 546/141

Primary Examiner—Glennon H. Hollrah
Assistant Examiner—James H. Turnipseed
Attorney, Agent, or Firm—Wegner & Bretschneider

[57] ABSTRACT

Heterocyclic amidoxime derivatives of the general formula:

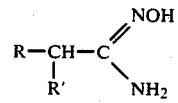

wherein R' represents hydrogen or the methyl radical, and R represents the 1-oxo-1H-isoquinolin-2-yl, 2-oxo-2H-quinolin-1-yl, 2,3-dihydro-1H-indol-1-yl, 1,3-dioxo-1,3-dihydro-2H-isoindol-2-yl, 1H-indol-1-yl, 1-oxo-1,3-dihydro-2H-isoindol-2-yl, 2-oxo-3,4-dihydro-2H-quinolin-1-yl, 5-chloro-3-methyl-2-oxo-2,3-dihydro-1H-benzimidazol-1-yl, 5-chloro-2-oxo-3-phenyl-2,3-dihydro-1H-benzimidazol-1-yl, 4-chloro-1-oxo-1H-isoquinolin-2-yl or 3-methyl-2-oxo-2,3-dihydro-1H-benzimidazol-1-yl radical, and—when R' represents the methyl radical—racemates and enantiomers of such compounds, are new compounds useful in therapy, and especially for the treatment of complaints of the central nervous system and for the treatment of depression.

7 Claims, No Drawings

ISOINDOLE AMIDOXIME DERIVATIVES

DESCRIPTION

This application is a divisional of Ser. No. 381,749, filed May 25, 1982, now U.S. Pat. No. 4,438,121.

The present invention relates to therapeutically useful heterocyclic amidoxime derivatives, to a process for their preparation and pharmaceutical compositions containing them.

Amidoximes useful in therapy have already been described in the literature, for example in U.S. Pat. Nos. 3,931,240, 3,984,470 and 4,265,911 and in British Pat. Nos. 1462311 and 2060606.

The amidoxime derivatives of the present invention are those compounds of the general formula:

$$R-CH(R')-C(=NOH)-NH_2 \quad (I)$$

wherein R" represents hydrogen or the methyl radical, and R represents the 1-oxo1H-isoquinolin-2-yl, 2-oxo-2H-quinolin-1-yl, 2,3-dihydro-1-H-indol-1-yl, 1,3-dioxo-1,3-dihydro-2Hisoindol-2-yl, 1H-indol-1-yl, 1-oxo-1,3-dihydro-2H-isoindol-2-yl, 2-oxo-3,4-dihydro-2H-quinolin-1-yl, 5-chloro-3-methyl-2-oxo-2,3-dihydro-1H-benzimidazol-1-yl, 5-chloro-2-oxo-3-phenyl-2,3-dihydro-1H-benzimidazol-1-yl, 4-chloro-1-oxo-1H-isoquinolin-2-yl or 3-methyl-2-oxo-2,3-dihydro-1H-benzimidazol-1-yl radical, and—when R' represents the methyl radical—racemates and enantiomers of such compounds. Also within the scope of the present invention are pharmaceutically-acceptable acid addition salts of the heterocyclic amidoxime derivatives.

Preferred compounds are those of general formula I wherein R' represents the methyl radical. Of particular interest are α-methyl-1-oxo-1H-isoquinolin-2-yl-acetamidoxime and 1-oxo-1H-isoquinolin-2-yl-acetamidoxime, and their pharmaceutically-acceptable acid addition salts.

According to a feature of the present invention, the heterocyclic amidoximes of general formula (I) are prepared by the reaction of a heterocylic compound of the general formula:

$$R-H \quad (II)$$

(wherein R is as hereinbefore defined) with a nitrile of the formula:

$$R'-CH(Cl)-CN \quad (III)$$

(wherein R' is as hereinbefore defined) in an organic solvent, for example dimethylformamide (abbreviated hereafter to DMF), in the presence of sodium hydride, and reaction of the resulting nitrile of the general formula:

$$R-CH(R')-CN \quad (IV)$$

(wherein R' and R are as hereinbefore defined) with hydroxylamine hydrochloride in an organic solvent, preferably an alcohol such as ethanol, in the presence of one equivalent of a base, for example sodium ethoxide.

The starting materials of formulae (II) and (III) are described in the literature.

Pharmaceutically acceptable acid addition salts of the amidoxime derivatives of general formula (I) can be obtained by methods known per se, for example by reacting the amidoxime with an acid, the anion of which is relatively innocuous to the animal organism in therapeutic doses of the salts, e.g. hydrochloric, methanesulphonic, fumaric or maleic acid.

The following non-limitative Example illustrates the preparation of amidoxime derivatives of general formula (I) by the process of the invention. The analyses and the IR and NMR spectra confirmed the structure of the compounds.

EXAMPLE

α-Methyl-1-oxo-1H-isoquinolin-2-yl-acetamidoxime (1) α-Methyl-1-oxo-1H-isoquinolin-2-yl-acetonitrile 3.4 g (0.07 mol) of a 50% dispersion of sodium hydride are introduced into a 250 ml round-bottomed flask; the sodium hydride is suspended in 50 cc of dry DMF, and a solution of 10 g (0.069 mol) of isocarboxtyril in 100 cc of dry DMF is added dropwise, with stirring and under dry nitrogen. The reaction is complete after stirring for one hour at ambient temperature.

The resulting solution is added dropwise to a solution of 7.16 g (0.08 mol) of 2-chloropropionitrile in 100 cc of dry DMF, cooled to −10° C. After stirring for one hour at −10° C., the reaction mixture is allowed to return to ambient temperature and left to stand overnight (under dry nitrogen). The DMF is evaporated off under reduced pressure and the residue is taken up in water and then extracted with diethyl ether. The organic phase, which is washed with water and then dried over MgSO$_4$, gives an oily residue, which is purified on a column [silica—CHCl$_3$/C$_6$H$_6$(5/5) and CHCl$_3$].

(2) α-Methyl-1-oxo-1H-isoquinolin-2-yl-acetamidoxime 9.8 g (0.049 mol) of the acetonitrile as obtained by step (1) and 3.5 g (0.05 mol) of hydroxylamine hydrochloride are introduced into a 500 ml round-bottomed flask together with 150 cc of absolute ethanol. A solution of sodium ethoxide, prepared by reacting 1.15 g of sodium (0.05 mol) with 50 cc of absolute ethanol, is added dropwise to the obtained suspension, with stirring under dry nitrogen. The mixture is then heated for 4 hours at the reflux temperature. After the ethanol has been evaporated, the residue is triturated in 100 cc of water. The product is washed 3 times with water and then dried. It is recrystallised from a mixture of EtOH/MeOH (8/2).

The product is obtained after filtration, washing with diethyl ether and drying at 60° C. in vacuo. Its melting point is 179°–80° C.

(3) Hydrochloride of the acetamidoxime

A slight excess of a solution of hydrogen chloride in diethyl ether is added to a suspension of 8 g (0.0346 mol) of the base obtained in step (2) in 100 cc of absolute ethanol. 100 cc of diethyl ether are added to the clear solution obtained and the product is left to crystallise, with stirring. The product is obtained after filtration, washing with diethyl ether and drying at 60° C. in vacuo. The melting point of the hydrochloride is 182°–5° C. (decomposition).

The following Table by reference to general formula (I) depicts the heterocyclic amidoxime derivatives obtained by the procedure of the foregoing Example and a similar procedure using appropriate starting materials of formulae (II) and (III).

TABLE

| Compound | R | R' | Melting point (°C.) |
|---|---|---|---|
| 1 | isoquinolin-1(2H)-one | CH₃ | Base: 179–180<br>HCl: 182–5 |
| 2 | quinolin-2(1H)-one | CH₃ | base: 187–8 |
| 3 | indoline | CH₃ | base: 150–1<br>HCl: 178–9 |
| 4 | phthalimide | CH₃ | base: 223–5 (decomposition) |
| 5 | indole | H | base: 138–9 |
| 6 | isoindolin-1-one | H | base: 210–12 (decomposition) |
| 7 | isoquinolin-1(2H)-one | H | base: 224–6 (decomposition) |
| 8 | isoindolin-1-one | CH₃ | base: 175–6 (decomposition) |
| 9 | 3,4-dihydroquinolin-2(1H)-one | CH₃ | base: 199–200 |
| 10 | 5-chloro-1-methylbenzimidazol-2(3H)-one | CH₃ | base: 210–11 |
| 11 | 5-chloro-1-phenylbenzimidazol-2(3H)-one | CH₃ | base: 160–161 |
| 12 | 4-chloroisoquinolin-1(2H)-one | CH₃ | base: 184–5 |
| 13 | 1-methylbenzimidazol-2(3H)-one | CH₃ | base: 185–6 |

The heterocyclic amidoxime derivatives of the present invention were subjected to pharmacological experiments.

The acute toxicity was determined on mice after intraperitoneal injection. The LD 50 is of the order of 200 to 1000 mg/kg animal body weight administered intraperitoneally.

The antidepressive activity was determined by the test for the antagonism towards the ptosis caused by reserpine (C. Gourat et al., J. Pharmacol. (Paris) 8, 333–350 (1977)).

The mice (male, CD1 Charles River, France, 18–22 g) simultaneously receive the products to be studied or the solvent (administered intraperitoneally), and the reserpine (4 mg/kg, administered subcutaneously).

After sixty minutes, the degree of palpebral ptosis is estimated for each mouse by means of a grading scale (0 to 4).

The average grading and the percentage variation relative to the control batch are calculated for each dose.

The AD 50, namely the dose which reduces the average ptosis score by 50% relative to the controls, is determined graphically for each product.

The AD 50 varies from 0.2 to 8 mg/kg animal body weight, administered intraperitoneally.

These data show that the compounds of the invention can be used for the treatment of various complaints, in particular for the treatment of various complaints of the central nervous system and for the treatment of depression.

The compounds of the invention can be presented in any form suitable for oral, parenteral or endorectal administration, for example in the form of tablets, coated tablets, coated pills, solutions to be taken orally or injected, etc., with any suitable excipient.

The daily doage of amidoxime derivative for an adult can range from 5 to 500 mg.

I claim:

1. A heterocyclic amidoxime derivative of the formula:

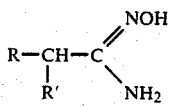

wherein
R' is a hydrogen atom or the methyl radical, and
R represents the 1,3-dioxo-1,3-dihydro-2H-isoindol-2-yl or 1-oxo-1,3-dihydro-2H-isoindol-2-yl radical, with the proviso that when R' represents the methyl radical, said derivative includes racemates and enantiomers thereof, and pharmaceutically acceptable acid addition salts thereof.

2. A heterocyclic amidoxime derivative according to claim 1 wherein R' represents the methyl radical.

3. 1,3-Dioxo-1,3-dihydro-2H-isoindol-2-yl-acetamidoxime.

4. 1-Oxo-1,3-dihydro-2H-isoindol-2-yl-acetamidoxime.

5. α-Methyl-1-oxo-1,3,-dihydro-2H-isoindol-2-yl-acetamidoxime.

6. A pharmaceutical composition which comprises, as active ingredient, a heterocyclic amidoxime derivative of the general formula depicted in claim 1, or a pharmaceutically-acceptable acid addition salt thereof, in association with any suitable excipient.

7. A method for the treatment of a patient suffering from a complaint of the central nervous system or for the treatment of depression which comprises administering to the patient an amount of a heterocyclic amidoxime derivative of the general formula depicted in claim 1, or a pharmaceutically-acceptable acid addition salt thereof, effective to ameliorate the condition of the patient.

* * * * *